United States Patent [19]

Zupancic et al.

[11] Patent Number: 4,614,770
[45] Date of Patent: Sep. 30, 1986

[54] NADHCN MIMICS AS CHIRAL PSEUDOCYANOTRANSFERASES

[75] Inventors: Joseph J. Zupancic, Bensenville; Raymond J. Swedo, Mount Prospect, both of Ill.

[73] Assignee: Allied Corporation, Morristown, N.J.

[21] Appl. No.: 736,049

[22] Filed: May 20, 1985

[51] Int. Cl.$^4$ ............................................. C08F 26/06
[52] U.S. Cl. ................................. 525/327.1; 525/375; 260/684; 526/259; 526/265; 435/183; 435/188; 435/193; 435/189
[58] Field of Search ............... 435/183, 188, 193, 189; 525/327.1, 375; 526/259, 265

[56] References Cited

U.S. PATENT DOCUMENTS 4,011,204  3/1977  Benes et al. ........................ 526/259

OTHER PUBLICATIONS

Talma et al., "Reduction of Activated Carbonyl Compounds with Bridged 1,4–Dihydropyridines", *J. Am. Chem. Soc.* 1985, vol. 107, pp. 3981–3997.

Chem. Abst. H. 109143e, vol. 85, 1976, Lehedena et al., "Kinetics of the Acylation of an Oxime Group, N–Methyl–4–Vinylpyridinium–Cl".

Kurimura et al., Effect of Polymeric Ligand on Electron Transfer Reaction", *J. Polymer Science*, vol. 9(12) 1971, pp. 3521–3527.

*Primary Examiner*—John Kight
*Assistant Examiner*—Garnette D. Draper
*Attorney, Agent, or Firm*—Thomas K. McBride; John F. Spears, Jr.; Eugene I. Snyder

[57] ABSTRACT

A broad class of polymers which mimic the NAD-NADHCN couple is disclosed. These polymeric pseudocyanotransferases may be used to effect asymmetric hydrocyanation of many types of carbonyl, thiocarbonyl, and imino groups in either a batch or continuous process, with the absolute configuration of the resulting optically active product predictable from the known absolute configuration of the chiral polymer.

8 Claims, No Drawings

NADHCN MIMICS AS CHIRAL PSEUDOCYANOTRANSFERASES

BACKGROUND OF THE INVENTION

Enzymes long have been recognized as stellar performers in the cosmos of life. As catalysts their efficiency and specificity are unmatched by man-made materials. As molecules their structure often is capable of a multitude of permutations to permit adaptation for functionality in differing species or on differing substrates. Although man has utilized enzymes to effect desired changes at least since the inception of recorded history (for example, in the production of fermented beverages) it is only relatively recently that he has achieved the first glimmerings of understanding how enzymes work.

That enzymes are produced only in living systems imposes various distinct limitations on their commercial use. For example, one such limitation is their production and supply; because they are efficient, enzymes usually are produced only in small amounts. If one desires to isolate a purified enzyme the situation is exacerbated since living systems generally secrete a large number of enzymes, so it is necessary to isolate a small quantity of one enzyme from a host of structurally related material of a different functionality. Another limitation is that use of an enzyme away from living systems often is difficult. In some cases this is not a serious limitation because the fermentation process is quite acceptable. More recently this limitation has been diminished using immobilized whole cells or the immobilized enzymes themselves to effect the desired chemical change. Yet another limitation is the enzymes' susceptibility to activity loss, generally by denaturation of the polypeptide or protein portion characteristic of enzymes. These limitations, among others, have provided an impetus to construct molecules which manifest the beneficial attributes of enzymes to the exclusion of their undesirable attributes.

Some enzyme systems require cofactors, or coenzymes, for the system to be operative. in a sense such systems have the additional limitation of requiring both an enzyme and its cofactor for the process to be carried out. In another sense such a system may provide the opportunity to use the cofactor, or an analogue, apart from the enzyme in a system where the enzyme's role can be readily played by a chemical reagent. Wheather it be the synthesis of a molecule showing enzyme properties or a molecule acting as a coenzyme, there is great motivation to construct mimics of biological catalysts.

This application relates to the preparation and use of enzyme mimics. In a narrower aspect it relates to enzyme analogue polymers, i.e., polymers operationally analogous to enzymes or coenzymes and which may, as in this case, be structurally analogous as well. More specifically, we are here concerned with polymers which are related to mimics of nicotinamide adenosine diphosphate and the use of a reduced form of such mimics, viz., dihydrocyanonicotinamide, in asymmetric reduction of carbonyl, thiocarbonyl, and imino groups in organic materials to form chiral L-hydroxynitriles, L-mercaptonitriles, and L-aminonitriles, resp.

For example, nicotinamide adenosine diphosphate (NAD) is a coenzyme for many dehydrogenases. NAD is readily reduced, the reduced form generally being abbreviated as $NADH_2$, and the $NAD-NADH_2$ pair acts as a redox couple for many substrates. This is schematically depicted below, where $SH_2$ and $S$ are the reduced and oxidized forms, respectively, of a suitable substrate.

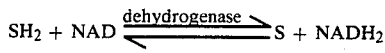

$$SH_2 + NAD \underset{}{\overset{dehydrogenase}{\rightleftharpoons}} S + NADH_2$$

That $NADH_2$ is the 1,4-reduction product of the nicotinamide portion of NAD is well accepted; thus, nicotinamide is the "active site" of the coenzyme.

In addition to the natural biological reduction, i.e., addition of hydrogen, of NAD to $NADH_2$, NAD also can react reversibly with HCN according to the equation,

$$NAD + HCN \rightleftharpoons NADHCN,$$

where NADHCN also is the 1,4-adduct of the nicotinamide portion of NAD. HADHCN can react with substrates containing a carbonyl, thiocarbonyl, or imino functionality by adding HCN to the latter. This cyanide transfer reaction is shown schematically as,

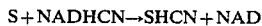

$$S + NADHCN \rightarrow SHCN + NAD$$

where S is a substrate bearing one of the aforementioned functional groups and SHCN is the resulting cyanohydrin.

The polymers of this invention are analogues of NAD and mimic the $NAD-NADH_2$ couple. The polymers are function analogues in readily shuttling between the unreduced and reduced forms. The polymers are structural analogues in containing modified nicotinamide as a recurring functional unit. The polymers *are not* analogues of NAD in that the reduced form of the polymer may be prepared in the absence of an enzyme and oxidation of the reduced form of the polymer, i.e., cyanide transfer to a substrate, also occurs in the absence of an enzyme.

The specificity of enzyme catalyzed reactions previously has been alluded to, and such specificity extends to stereospecificity in the sense that only one of many enantiomers of a chiral material may be a suitable substrate, or only one of several enantiomers may be the product of enzyme catalyzed transformation. Such stereospecificity extends to $NAD-NADH_2$ where two D-ribose units provide an asymmetric environment. In this invention we have provided polymeric enzyme analogues with an asymmetric environment in close proximity to the amide nitrogen of the nicotinamide and nicotinamide-like recurring units, with the result that the reduced form of the polymer effects asymmetric reduction of suitable substrates, including the carbonyl group of aldehydes and ketones, the thiocarbonyl group of thioaldehydes and thioketones, and the imino group of imines. In short, the polymers described herein are mimics of the NAD—NADHCN system where the reduced form serves as a chiral pseudocyanotransferase for substrates containing the aforementioned functional groups.

DESCRIPTION OF THE INVENTION

The polymers of this invention have a backbone to which are attached pendant modified nicotinamide residues which are covalently bonded to a carbon of the backbone through the ring nitrogen of such nicotinamide. Quite diagramatically, the polymers may be represented as

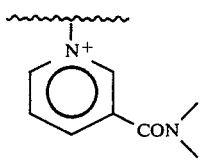

where ⁓⁓⁓⁓ represents a polymer backbone.

In one sense, any polymeric backbone providing a covalent source of attachment to the ring nitrogen of the modified nicotinamides used in this invention are suitable. However, we believe it is advantageous to use homopolymers and copolymers of styrene containing a functionalized methyl group at its 3 or 4 position, i.e., styrenes of the structure

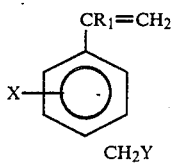

The functionalized methyl group of the styrenes react with the ring nitrogen of the nicotinamides used herein, thus serving as one terminus of the covalent attachment. The group Y is most often a halogen, excluding fluorine, but may be any other group which can be replaced in a nucleophilic substitution by the ring nitrogen of nicotinamides. Thus, Y also may be a sulfonate ester, such as the mesylate or p-toluene sulfonate ester, activated carboxylate esters, such as p-nitrobenzoate, 2,4-dinitrobenzoate, and other leaving groups too well known in nucleophilic displacement reactions to require extensive description.

The homopolymers may arise from a functionalized 3- or 4-methylstyrene itself or from a substituted 3- or 4-methylstyrene. Such substituents may appear at the alpha-position, i.e., $R_1$ is different from H, or the substituents may be on the ring. Where an alpha-substituent, $R_1$, is present it is usually an alkyl group, especially a lower alkyl group containing up to about 5 carbon atoms. Where a ring substituent, X, is present the only requirement is that it be inert both in the context of polymerization and in the context of the chemical properties of the resulting polymer. Examples of such substituents include alkyl groups, halogens, alkyl ethers, aryl ethers, tertiary amines, and quaternary amines.

Where the polymeric backbone of this invention is a copolymer of styrene, the styrene conforms to the description given above and the copolymer may be any vinyl monomer, $R_2R_3C=CH_2$. The exact nature of the vinyl monomer is unimportant except to the extent that it be capable of forming a copolymer with the styrene used. Examples of suitable copolymers include ethylene, propylene, 1,1-dichloroethylene, acrylonitrile, the acrylates, vinyl toluene, vinyl chloride, and so forth. The materials which form the polymeric backbone of this invention may be crosslinked where it is desired that the final polymeric product of this invention be insoluble. The resulting copolymers, I, without regard to extent of crosslinking, are

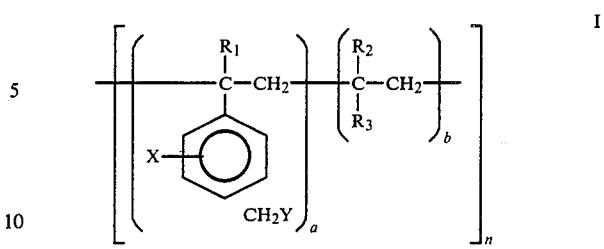

where, for reasons to be elaborated upon within, a is an integer from 1 to 4, preferably 1 or 2, and b is an integer from 2 to 8, better from 3 to 7, and best from 4 to 6 where a is preferably 2 and at least 4 where a is preferably 1, $R_2$, $R_3$ are independently selected from the group of $R_1$ and halogen, and n is a large integer representing the degree of polymerization.

Other materials suiable as the polymeric backbone of this invention are copolymers of a vinyl monomer, as described above, and stilbene or acenaphthylene containing a functionalized methyl group at an appropriate position. The resulting structures of these materials are IIa and IIb, respectively.

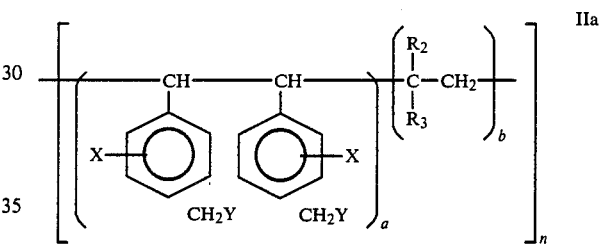

where a is an integer up to 3, but most preferably 1, and b is an integer from 3 to 7, and preferably from 4 to 6.

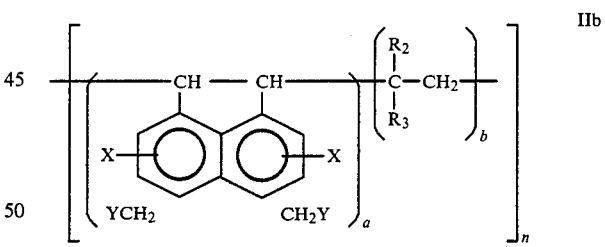

Attached to the polymer backbone is a heterocycle which is a nicotinamide residue, or an aromatic ring system incorporating the pyridine nucleus and bearing mono- or disubstituted carboxamido groups at the 3- or 3,5-positions relative to the pyridine ring nitrogen, with the attachment being by a covalent bond between an atom of the polymer backbone and the nitrogen atom of the pyridine ring system. The purpose of the fuctionalized methyl group on the aromatic residues of the polymeric backbones described above is to provide a reactive center which engages in the aforementioned bonding.

In the simplest case the heterocycle is nicotinamide itself, 3-pyridylcarboxamide, where the amide is either monosubstituted or disubstituted,

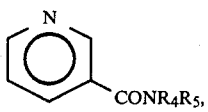

$R_5$ is not equal to H if $R_4$ is equal to H.

Another heterocycle which may be used in this invention is the diamide of 3,5-pyridinedicarboxylic acid where each amide is at least monosubstituted,

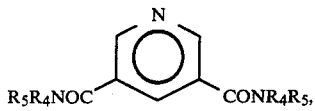

$R_5$-H if $R_4$=H.

Fused ring systems incorporating the pyridine nucleus also may be used in the practice of this invention. Examples include the mono- or disubstituted amides of 3-quinolinecarboxylic acid, 4-isoquinolinecarboxylic acid and 4,6-isoquinolinedicarboxylic acid.

In the carboxamide groups present at the 3- or 3,5-positions, relative to the ring nitrogen, of the aromatic heterocycles of this invention $R_4$, $R_5$ are selected from the group consisting of hydrogen and alkyl or substituted alkyl groups subject to the constraint that not more than one of $R_4$, $R_5$ is hyrogen and at least one of the alkyl or substituted alkyl groups has a chiral center adjacent to the nitrogen, i.e., it is bonded to the amide nitrogen via a chirotopic carbon atom. Examples, which are to be emphasized are illustrative only, of suitable $R_4$, $R_5$ groups which may be alkyl, cycloalkyl, aralkyl, and substituted derivatives thereof, include 1-phenylethyl, 1-(1-phenyl)propyl, 1-(1-naphthyl)ethyl, 1-(2-naphthyl)ethyl, menthyl, 1-carbamoylethyl, 1-(1-carbamoyl)propyl, 1-(1-carbamoyl-2-methyl)propyl, 1-(1-carbamoyl-2-phenyl)ethyl, 1-(1-carbamoyl-3-methyl)butyl, 1-(carbomethoxy-3-methyl)butyl, 1-(1-carbamoyl-2-p-methoxyphenyl)ethyl, and so on.

The groups $R_4$ and $R_5$ also may be part of a cyclic system which incorporates the amide nitrogen. Examples of such systems include pyrrolidines and piperidines generally, especially

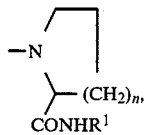

where n is 1 or 2 and $R^1$ is an alkyl group, especially a lower alkyl containing up to about six carbon atoms, or an aralkyl moiety, and such diverse ring systems as 1,3-diazacyclopentane, 1,3-diazacyclohexane, 1,4-diazacyclohexane, 1-oxa-4-azacyclohexane, 1-thia-3-azacyclopentane, 1-thia-3-azacyclohexane, and so forth.

Particularly favored are those materials where at least one of $R_4$, $R_5$ is a residue of an alpha-amino acid ester, especially those of naturally occurring amino acids. That is, $H_2NR_4$ or $H_2NR_5$ is an ester of an alpha-amino acid where $H_2N$ is the amino group of the acid. For example, where alanine is the alpha-amino acid $R_4$=—$CH(CH_3)CO_2CH_3$, using the methyl ester to illustrate this case. The use of alpha-amino acids is especially favored in the case of monosubstituted amides, i.e., $R_4$ is hydrogen, so that —$NHR_5$ is an alpha-amino acid ester minus a hydrogen of the amino group. In the usual case the alpha-amino acid ester will be that of a naturally occurring D- or L-amino acid, because of their greater availability. However, it should be apparent that our invention is not restricted to such alpha-amino acids, and that in fact it encompasses all alpha-amino acids whose amino carbon is chirotopic. Examples of suitable amino acids include alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, phenylglycine, and valine.

Where the heterocycle has two carboxamido groups at the 3,5-positions relative to the ring nitrogen atom, a cyclic structure incorporating the amino groups is preferred. This is exemplified in the structure below which uses pyridine as the ring system for convenience only.

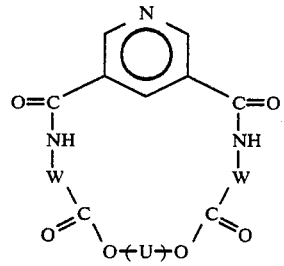

The residue —NH—W—$CO_2$— is that of an alpha-amino acid as described above, preferably a naturally occurring one, where H(—$NHWCO_2$—)H is said amino acid. Therefore, these materials are cyclic esters of 3,5-dicarboxylic acid amides where each amide arises, at least conceptually, from an alpha-amino acid. Lysine, phenylalanine, and valine are especially favored amino acids in this branch of the invention.

The group designated as U is a spacer; i.e., it functions only to maintain a desired spatial relationship in the resulting macrocyclic ring system. Among suitable groups which may function as the spacer may be mentioned polymethylene, $(CH_2)_p$, where p is an integer from about 4 to about 10; a polyoxyethylene, —$CH_2CH_2(OCH_2CH_2)_q$—, where q is 2 or 3; and the entities

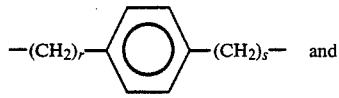 and

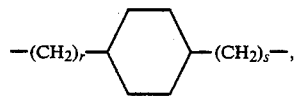

where r and s are integers such that r+s is from 2 to about 6.

Where the amide functionality is not part of a macrocyclic system, the heterocyclic rings may occur singly separated by about 4 vinyl monomeric units, or in pairs with the minimum spacing possible between them, each pair being separated by approximately 5 vinyl monomeric units. Where the amide functionality is part of a macrocyclic ring system, it is best that the heterocyclic ring system of the polymer be separated by at least about 4 vinyl monomeric units.

Where the polymeric backbone is IIa, and the heterocyclic amide is exemplified by a nicotinamide, the polymers of this invention have the structure

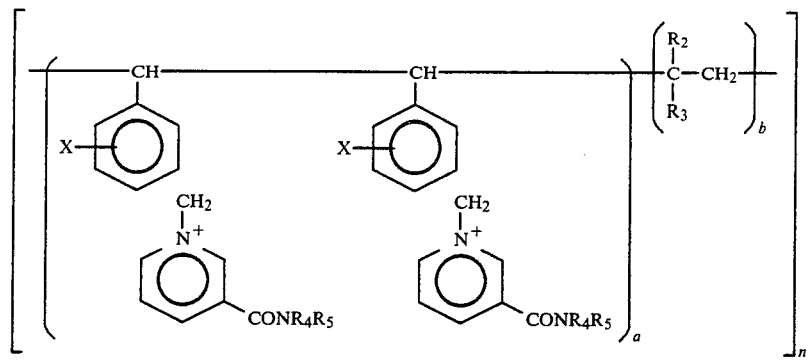

To summarize, using homopolymers and copolymers I as the polymeric backbone and nicotinamide to exemplify a monoamide of a heterocyclic ring system, the polymers of this invention would have the structure,

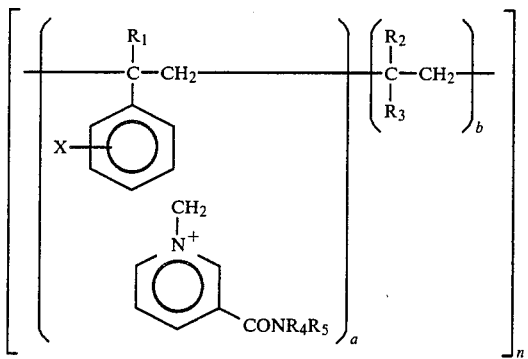

where $a=2$, $b=4-6$ in the preferred case, with a being an integer from 1 to 4, and b being either zero (homopolymers) or an integer from 2 to 8 in the general case.

Where the polymeric backbone is I and the heterocyclic aromatic amide is a dicarboxylic acid amide incorporated into a macrocyclic structure, the polymers of this invention would have the structure,

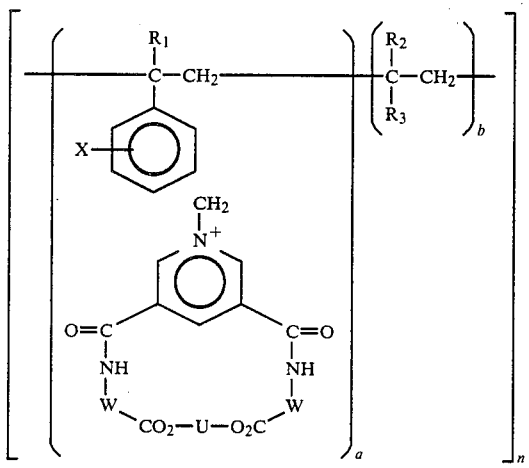

where $a=1$ and b is an integer at least 4.

where in the preferred case a is 1 and b is an integer from 4–6.

Where the polymeric backbone is IIB, and the heterocyclic amide is exemplified by a nicotinamide, the polymers of this invention have the structure

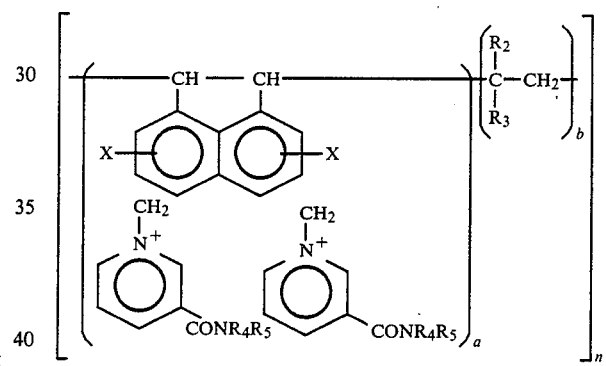

where in the preferred case a is 1 and b is in integer from 4–6.

The reduced form of the polymer is the cyanide transfer agent in the process of this invention. The reduced form of the polymer is the neutral form of the 1,4-addition product of hydrogen cyanide and is exemplified by the following reaction, where Ⓟ represents the polymer backbone used in this invention.

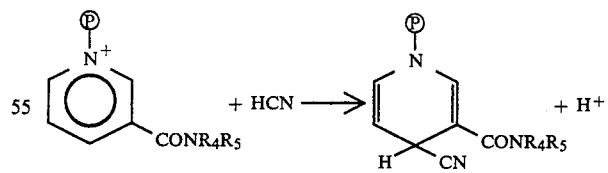

Any reagent affording the desired 1,4-addition product may be used in the formation of the reduced form of the polymers of this invention. The best reagents are inorganic cyanide salts, such as sodium, potassium, and ammonium cyanide. Preparation of the reduced form is relatively straightforward and can be effected by reacting a solution of the polymer with an aqueous solution of a suitable cyanide salt followed by removal of solvent and washing the adduct with, for example, methanol or ethanol.

The reduced form of the polymer, optionally in the presence of certain metal cations, will effect hydrocyanation of the carbonyl group of ketones and aldehydes, the thiocarbonyl group of thioketones and thioaldehydes, and the imino group of imines to hydroxynitriles, mercaptonitriles, and aminonitriles, respectively. Because the polymer in its reduced form has a chiral center near the active site, the cyanide transfer, or hydrocyanation, is asymmetric, i.e., the products are optically active where introduction of a chiral center accompanies cyanide transfer. Where $R_4$ or $R_5$ is from an L-amino acid derivative, which has the S configuration, the product will have the S configuration. The organic nitriles can be hydrolyzed under nonracemizing conditions, the products from aldehydes and ketones ultimately affording L-hydroxycarboxylic acids, the products from thio aldehydes and ketones affording L-mercaptocarboxylic acids, and those from imines leading to L-aminocarboxylic acids.

The cyanide transfer reactions can be effected in the absence or presence of metal cations, but not necessarily with equivalent results. The cations which may be used in the practice of this invention include the divalent cations of magnesium and zinc for the reduction of the carbonyl or thiocarbonyl groups, and the monovalent cation of lithium for the reduction of imines. The purpose of the metal is to complex with the nitrogen of the amide groups of the polymer and the oxygen, sulfur, or nitrogen of the carbonyl, thiocarbonyl, or imino group to be reduced. In the absence of the metal cations reduction occurs quite slowly. Where the polymers have an acyclic amides system about two molar proportions of monovalent cation and one molar proportion of divalent cation is needed for complete or near complete complexation. Where the amide is incorporated in a macrocyclic ring system, about one molar proportion of the monovalent cation and 0.5 molar proportion of the divalent cation are needed. In all cases molar proportions are relative to the heterocyclic aromatic amide units in the polymer. Complexation usually results by merely contacting an aqueous or partly aqueous solution of the cation with the reduced form of the polymer.

The substrates of this invention are organic materials having reducible carbonyl, thiocarbonyl, or imino groups associated with aldehydes, ketones, thioaldehydes, thioketones, and imines, respectively. Such functional groups are converted to hydroxynitriles, mercaptonitriles, and aminonitriles.

Three factors affect reaction: (1) equilibrium of the NAD—NADHCN couple, (2) steric effects and (3) redox potential. The equilibrium of the NAD—NADHCN couple will be affected by solvent, ionic strength, and type of surfactant employed. The steric effects will effect the strength and extent of substrate-NADHCN interaction. Finally, the redox potential of the functional group and its hydrocyanated counterpart and the redox potential of the polymer and its reduced form will determine the rate of reaction.

The process of this invention may be effected by contacting the reduced form of the polymer, either free of metals or complexed with an appropriate divalent or monovalent metal cation, with a solution of the organic substrate containing the reducible functional group in a nonaqueous but water-miscible organic solvent otherwise inert under the reaction conditions. Examples of such organic solvents include alcohols, nitriles, hexamethylphosphoramide, dimethylformamide, dimethylacetamide, N-methylacetamide, tetrahydrofuran, tetrahydropyran, and dioxane, to cite but a few.

The reduced form of the polymer always will be insoluble in the organic solvents of this invention. However, the polymer itself may be either soluble or insoluble, a distinction which may influence the details of the cyanide transfer process. For example, if the polymer is soluble it is first converted to the reduced form by contact with a solution of a suitable cyanide salt, such as sodium cyanide. The reduced form then is collected and if desired complexed with an appropriate metal cation by contacting the reduced form with a sufficient amount of an aqueous solution of a metal cation to complex a substantial portion of the amide functions in the polymer. After any excess of solution containing the metal cation is removed, the reduced and complexed form of the polymer is contacted with a solution of the organic substrate in a nonaqueous but water-miscible organic solvent. As the reaction proceeds the mixture tends to become homogeneous by conversion of the insoluble, reduced form of the polymer to the soluble polymer itself. The reduction products are then separated from the polymer by conventional means, which normally entails insolubilizing the polymer. Often this is done by the addition of small amounts of water to precipitate polymer while leaving the reduced organic substrate in solution. Solids are then removed, and from the filtrate there is recovered the reduced organic material by suitable means as by distillation, fractionation, and so forth.

Where the polymer itself is insoluble cyanide transfer may be performed using the polymer in its reduced form as a bed in a semicontinuous regenerative process. For example, a bed of the polymer may be transformed to its reduced form by passing through the bed sufficient quantity of a solution of, for example, potassium cyanide to effect more or less complete 1,4-addition. After excess cyanide solution is drained, the bed is washed with alcohol, followed by a methanol or ethanol wash. Where desired, the bed may be contacted with a solution of metal cation to complex at least a substantial portion of the amide groups present. Thereafter, a solution of the organic substrate in a nonaqueous but water-miscible organic solvent may be passed through the column at a rate to effect complete or near complete reduction of the reducible functional groups born by the organic substrate. The solution of organic material also may contain sufficient divalent metal cation to replace that which may otherwise be leached from the column during reduction. The effluent is then collected and the reduced organic substrate separated therefrom by conventional means, as by distillation, solvent fractionation, and so forth.

The examples given below are intended to be illustrative only and are not to be construed as limiting the invention in any way.

EXAMPLE 1

N-((S)-α-Methylbenzyl)nicotinamide: 14.2 g (0.10 mols) of nicotyl chloride in 200 ml of methylene chloride was charged into a 500 ml round bottom flask equipped with condenser, addition funnel, thermometer, drying tube, $N_2$-purge and magnetic stirrer, and to the cooled (5° C.) stirred reaction mixture was added dropwise over a 3 hour period a 100 ml methylene chloride solution of 15.0 g (0.124 mols) of (S)-α-methylbenzylamine and 35 ml of triethylamine. The stirred reaction mixture was warmed to 25° C. over a 16 hour period. The solvent was stripped from the reaction mixture under vacuum and the resulting white solid was digested with 660 ml of 1.1M HCl. The aqueous solution was treated with Norit and filtered, then neutralized to pH 7.0 with sodium carbonate. This solution was washed twice with methylene chloride, the washings were combined and then washed three times with a sodium bicarbonate solution and twice with water. The organic solution was dried over sodium sulfate, filtered and concentrated under vacuum to yield a yellow oil. The product was crystallized from benzene to yield 12.1 g (0.054 mols), m.p. 88°–89° C.

EXAMPLE 2

Bis(S-phenylalanine)-3,5-pyridinecarboxamide: 150 ml of a 2N sodium hydroxide solution was charged into a 500 ml round bottom flask equipped with condenser, addition funnel, thermometer, and magnetic stirrer. To the stirred, cooled (15° C.) solution was added 14.52 g ($8.80 \times 10^{-2}$ mols) of L-phenylalanine, and the solution was then cooled to 5° C. To the stirred reaction mixture was added, dropwise over a 1.5 hour period at 5° C., 200 ml methylene chloride containing 7.60 g ($4.0 \times 10^{-2}$ mols) of 3,5-pyridinedicarboxylic acid chloride. After the reaction mixture was stirred for 1 hour at 5°–10° C., it was transferred to a separatory funnel and the organic phase was separated. The aqueous phase was washed with methylene chloride and then acidified to pH 4.0 with formic acid with formation of a white crystalline solid. After isolation and purification, the product yield was 16.78 g ($3.64 \times 10^{-2}$ mols).

(4S-(4S*,15S*))-4,15-Bis(phenylmethyl)-2,5,14,17-tetraoxo-6,13-dioxa-3,16,20-triazabicyclo-(16.3.1)docosa-1(22),18,20-triene: A mixture of 4.62 g ($1.00 \times 10^{-2}$ mols) of bis(S-phenylalanine)-3,5-pyridinedicarboxamide and 3.60 ($1.10 \times 10^{-2}$ mols) of cesium carbonate were suspended in 400 ml of DMF (freshly distilled) in a 1 liter 4-neck round bottom flask equipped with condenser, addition funnel, thermometer, drying tube, nitrogen purge and magnetic stirrer. The stirred reaction mixture was gently heated to 50° C. and then a 125 ml DMF solution of 2.55 g ($1.05 \times 10^{-2}$ mols) of 1,6-dibromohexane was added dropwise over a 4 hour period. The reaction mixture was maintained at 50° C. with stirring for 64 hours. The cooled reaction mixture was concentrated under vacuum. The yellowish oil was dissolved into 300 ml of water and 300 ml of methylene chloride. The organic phase was separated, dried over sodium sulfate and concentrated under vacuum. After recrystallization from methylene chloride:ether the product yield was 0.90 g ($1.66 \times 10^{-3}$ mols).

EXAMPLE 3

1-(Vinylbenzyl)-3-((S)-α-methylbenzylcarbamoyl)-pyridinium chloride: A 100 ml methanol solution containing 2.26 g ($1.00 \times 10^{-2}$ mols) of N-((S)-α-methylbenzyl)nicotinamide was charged into a 250 ml round bottom flask equipped with condenser, addition funnel, drying tube, nitrogen purge and magnetic stirrer. To this stirred reaction mixture was added, dropwise over a 10 minute interval, 50 ml of a methanol solution containing 1.53 g ($1.00 \times 10^{-2}$ mols) of chloromethylstyrene. The solution was stirred for 24 hours at 25° C., then was concentrated under vacuum to afford solid which was recrystallized from methanol to yield 3.40 g ($8.98 \times 10^{-3}$ mols) of product.

EXAMPLE 4

Poly(1-(vinylbenzyl)-3-((S)-α-methylbenzylcarbamoyl)-pyridinium chloride-styrene): 3.40 g ($8.98 \times 10^{-3}$ mols) of 1-(vinylbenzyl)-3-((S)-α-methylbenzylcarbamoyl)-pyridinium chloride, 10.4 g ($5.00 \times 10^{-2}$ mols) of styrene and 0.05 g of AIBN in 200 ml of ethanol were charged into a 500 ml round bottom flask equipped with condenser, drying tube, and magnetic stirrer. The reaction mixture was refluxed for 24 hours. The polymer was coagulated from solution by addition to water. The polymer was washed and then dried overnight in a vacuum desiccator to afford 7.0 g of polymer.

The activity of the polymer, i.e., NAD content, was examined by its ability to reduce methylene blue after treatment with sodium dithionite. To 0.50 g of polymer suspended in 50 ml of water in a 250 ml round bottom flask equipped with nitrogen purge and magnetic stirrer was added 40 ml of a $4.08 \times 10^{-1}$M sodium dithionite, $3.69 \times 10^{-1}$M potassium carbonate solution ($CO_2$ saturated). The polymer took on a yellow color immediately and was stirred for 10 minutes at ambient temperature. The reduced polymer was collected by filtration and washed repeatedly with water until washings failed to reduce methylene blue indicator solution. The polymer was suspended in a solution of 25 ml water and 10 ml ethanol in a 250 ml round bottom flask equipped with nitrogen purge and magnetic stirrer. This reaction mixture was titrated with a $7.81 \times 10^{-3}$M methylene blue solution. The $NADH_2$ activity was 0.9 mequiv/g polymer.

EXAMPLE 5

Poly(20-(vinylbenzyl)-((4S-(4S*,15S*))-4,15-bis(phenylmethyl)-2,5,14,17-tetraoxo-6,13-dioxa-3,16,20-triazabicyclo(16.3.1)docosa-1(22)18,20-triene)-styrene) resin: 50.0 g of poly(styrylmethylene chloride) resin, 2.0% crosslinked, 1 mg Cl/g was cleaned by washing with 2-butanone and then twice with 200 ml of a 5% HCl solution in 2-butanone. The resin was washed with 2-butanone until washings were nonacidic (pH 6.0). The resin was dried overnight in a vacuum oven at 60° C.

The above resin, 3.0 g, was suspended in 50 ml of dry dioxane in a 500 ml round bottom flask equipped with condenser and drying tube. To the above solvent swollen polymer was added 0.9 g ($1.66 \times 10^{-3}$ mols) (4S-(4S*,15S*))-4,15-bis(phenylmethyl)-2,5,14,17-tetraoxo-6,13-dioxa-3,16,20-triazabicyclo(16.3.1)docosa-1(22),18,20-triene. The reaction mixture was heated under reflux for four days. The cooled reaction mixture was filtered and the resin washed with p-dioxane and then dried overnight. The activity of the polymer was assayed with methylene blue as in the above example; $NADH_2$ activity 0.4 mequiv/g of polymer.

EXAMPLE 6

Generation and Use of NADHCN mimic: The NADHCN mimic polymer can be utilized in either a batch or continuous (bed) process. The generation of the active NADHCN moiety from the NAD species and its subsequent use are identical, differing only in how the coenzyme mimic is implemented in use.

The reduction of the NAD moiety of the polymer to the NADHCN moiety can be effected by treating the polymer as follows in an inert atmosphere (i.e. $N_2$, $CO_2$, etc.).NAD-containing polymer, 3.00 g, may be treated with 50 ml of water containing 0.50 g of benzyltrimethylammonium chloride at 25° C. for 0.50 hrs. To this rection mixture can be added a 50 ml aliquot of $5.00 \times 10^{-1}$M potassium cyanide. After 15–30 minutes of treatment the aqueous solution can be removed and the polymer washed with water until washings fail to indicate cyanide with silver nitrate or ferrous sulfate. The polymer may then be washed with ethanol to remove water.

To the ethanol treated NADHCN containing polymer may be added 0.50 g phenylacetaldehyde in 50 ml of ethanol and either stirred with the polymer or pumped over the polymeric resin bed. After approximately 24 hrs. the NAD containing polymer may be washed with ethanol, the NADHCN moiety regenerated, and the reaction medium reintroduced. This process may be repeated until the substrate (i.e. phenylacetaldehyde) is completely reduced, based upon the activity of the polymer. The ethanol solution may be concentrated under vacuum to yield product after workup.

What is claimed is:

1. A method of asymmetric hydrocyanation of the carbonyl group of aldehydes and ketones, the thiocarbonyl group of thioaldehydes and thioketones, and the imino group of imines comprising reacting a solution in a nonaqueous but water-miscible organic solvent of an organic substrate containing a reducible carbonyl, thiocarbonyl, or imino group with the reduced form of a polymer to whose backbone is attached an aromatic heterocyclic ring system having a pyridine nucleus and bearing mono- or disubstituted carboxamido groups at the 3- or 3,5-positions relative to the pyridine ring nitrogen, said attachment being a covalent bond between a carbon atom of the polymer backbone and the pyridine ring nitrogen, where the aromatic heterocyclic ring system is a pyridine, quinoline, or an isoquinoline ring system, and said carboxamido group has the formula —CONR$_4$R$_5$, where R$_4$, R$_5$ is selected from the group consisting of hydrogen and alkyl, aralkyl, substituted alkyl or substituted aralkyl groups subject to the constraint that not more than one of such groups is hydrogen and at least one of the alkyl, aralkyl or substituted alkyl or aralkyl groups has a chiral center adjacent to the nitrogen of the amide and separating the reduction product produced thereby and the polymer.

2. The method of claim 1 where the aromatic heterocyclic ring system is a pyridine.

3. The method of claim 2 where the pyridine contains a mono- or disubstituted carboxamido group at the 3-position.

4. The method of claim 2 where the pyridine contains a mono- or disubstituted carboxamido group at both the 3- and 5-positions.

5. The method of claim 1 where the carboxamido groups are incorporated into a macrocyclic ring system of formula

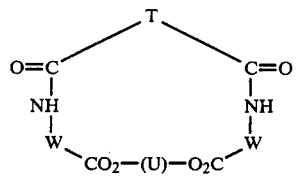

where T is a pyridine, quinoline, or isoquinoline ring system, W is a portion of an alpha-amino acid of the formula H$_2$N(W)CO$_2$H with a chiral center adjacent to nitrogen, said amino acid selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, phenylglycine, and valine and U is selected from the groups consisting of —(CH$_2$)$_p$—, where p is an integer from about 4 to about 10, —CH$_2$CH$_2$—(OCH$_2$CH$_2$)$_q$—, where q is 2 or 3, and —(CH$_2$)$_r$—M—(CH$_2$)$_s$—, where M is a 1,4 divalent cyclohexane or benzene radical and r, s are integers such that r+s is from 2 to about 6.

6. The method of claim 1 where R$_4$ is hydrogen and R$_5$ is a portion of an alpha-amino acid such that H$_2$NR$_5$ is an alpha-amino acid.

7. The method of claim 6 where the alpha-amino acid is selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, phenylglycine, and valine.

8. The method of claim 1 where the reaction is effected in the presence of the divalent cation of magnesium or zinc or the monovalent cation of lithium.

* * * * *